United States Patent
Campbell et al.

[11] Patent Number: 6,077,237
[45] Date of Patent: Jun. 20, 2000

[54] HEADSET FOR VESTIBULAR STIMULATION IN VIRTUAL ENVIRONMENTS

[75] Inventors: Craig Campbell; William Heckel, both of Pittsburgh, Pa.

[73] Assignee: Adaboy, Inc., Pittsburgh, Pa.

[21] Appl. No.: 09/187,759

[22] Filed: Nov. 6, 1998

[51] Int. Cl.[7] ................................. A61B 5/103
[52] U.S. Cl. ........................ 600/587; 600/595; 607/139
[58] Field of Search .................... 600/558, 559, 600/587, 595; 607/55, 56, 136, 137, 115, 139; 345/7, 8

[56] References Cited

U.S. PATENT DOCUMENTS

| | | | |
|---|---|---|---|
| 4,558,703 | 12/1985 | Mark | 128/421 |
| 4,667,676 | 5/1987 | Guinta | 128/419 R |
| 4,830,024 | 5/1989 | Nashner et al. | 600/595 |
| 4,918,757 | 4/1990 | Janssen et al. | 2/171 |
| 5,323,468 | 6/1994 | Bottesch | 381/151 |
| 5,373,857 | 12/1994 | Travers et al. | 128/782 |
| 5,479,934 | 1/1996 | Imran | 600/390 |
| 5,515,078 | 5/1996 | Greschler et al. | 345/156 |
| 5,572,749 | 11/1996 | Ogden | 2/421 |
| 5,593,432 | 1/1997 | Crowther et al. | 607/46 |
| 5,726,916 | 3/1998 | Smyth | 364/559 |
| 5,737,505 | 4/1998 | Shaw et al. | 395/119 |
| 5,740,812 | 4/1998 | Cowan | 128/732 |
| 5,762,612 | 6/1998 | Campbell | 600/558 |
| 5,767,820 | 6/1998 | Bassett et al. | 345/8 |
| 5,771,298 | 6/1998 | Davis et al. | 600/25 |
| 5,877,732 | 3/1999 | Ziarati | 600/418 |
| 5,983,129 | 11/1999 | Cowan et al. | 600/545 |

*Primary Examiner*—Max Hindenburg
*Assistant Examiner*—Charles Marmor, II
*Attorney, Agent, or Firm*—Kenneth P. McKay, Esq.

[57] ABSTRACT

A headset to accompany virtual reality units which provides a user the sensation of motion by vestibular stimulation. A fixed or adjustable device positions conductors on the forehead and mastoid regions of the user's head capable of receiving computer generated electrical currents that may be synchronized to audio or video displays to enhance the effect of virtual environments by causing dysequilibrium and a resulting sensation of motion therein.

2 Claims, 3 Drawing Sheets

6,077,237

HEADSET FOR VESTIBULAR STIMULATION IN VIRTUAL ENVIRONMENTS

FIELD OF THE INVENTION

The invention relates to a virtual reality headset that employs a means of stimulating the vestibular system of the inner ear, thereby intensifying the realism of virtual reality by providing a sense of movement and dysequilibrium within virtual reality environments.

DESCRIPTION OF THE RELATED ART

Early in the development of virtual reality systems, head-tracking apparatuses were developed which could determine the orientation of the head in virtual environments, relative to the earth's magnetic field. Head movement resulting from response to stimulus could provide a new visual stimulus in the use of virtual reality demonstrations.

Today's virtual reality systems provide head mounted visual display units which provide the wearer a view of the three dimensional virtual reality world, while at the same time visually displaying both head and limb movement. Support members on head-mounted shells allow for the attachment of video display units, enabling a person to view his or her movements in accordance with their own actual movements, as seen in U.S. Pat. No. 5,767,820. Noticeably, in these systems, the emphasis lies in the user's view of the virtual universe as it changes with the motion of his or her head. This system provides a user only visual stimuli, however, as no actual sensation of motion is realized through the use of this display unit.

Recently, the sense of touch has been introduced in virtual reality (U.S. Pat. No. 5,737,505). A method is provided for entering user position into a virtual reality realm and providing tactile feedback from that virtual reality. A user can feel interactions with objects represented in the virtual environment viewed through a head device which includes a display means comprising video goggles. A user can view his or her simulated motion, as well as "feel" computer generated objects. However, this sense of touch is obtained only through physical movement within a complex head, chest, and arm outfit. Again, as well, the motion of the user is only viewed through the head apparatus, and cannot be felt.

Obviously, the current state of virtual reality is limited by stimulation of the visual scene as it relates to head worn units. Other sensations have been implemented, yet they involve complex, costly outfits and do not account for the feel of actual motion when visual displays are used. Motion sensation can obviously be coupled to visual or audio stimuli by use of an expensive and cumbersome mechanical chair or seat that rotates or rocks in synchronization to the display. The instant invention provides stimulation to the vestibular sensory system to provide a user the actual sensation of motion associated with balance and position in virtual reality environments without mechanical influences upon inertia. The instant invention is a headset that is worn to provide the feel of motion while coupled to visual and/or audio stimuli.

Methods for stimulating the vestibular system currently exist. These methods are used in physiological evaluation and testing, and for the alleviation of pain and withdrawal symptoms of a patient during the detoxification process. Different methods and apparatuses treat motion sicknesses and nausea. These developments, however, do not emphasize the capability of stimulating the vestibular system in such a way as to synchronize audio and visual displays in virtual reality environments with the sensation of motion. The enhanced virtual reality system employing vestibular stimulation is now taught by U.S. Pat. No. 5,762,612 (Campbell). The galvanic electrodes are pasted on or near the mastoid bone of each ear to produce the dysequilibrium sensation. Although the location of the electrodes is disclosed therein, and also in U.S. Pat. No. 5,323,468 for the purpose of transmitted audio media, optimal placement and a means of enhancing contact with the area for electrical conduction to accompany virtual reality is now disclosed and taught herein. The instant invention improves on the Campbell patent by demonstrating a means of easily contacting electrical conductive electrodes on or near the mastoid bones and forehead, thereby providing the necessary placement and compression to allow for optimal vestibular stimulation.

The balance center of the ear is known as the vestibule. The vestibular apparatus is known to consist of the inner ear structures that are associated with balance and position sense. It includes the vestibule and the semicircular canals. Conductive material situated on the headset, and, accordingly, placed on the mastoid bone behind each ear and on the forehead provides the stimulation to the vestibular apparatus. Passing small currents between these headworn electrodes is computer generated and controlled to accompany the relative velocity and acceleration cues in virtual reality environments or video displays. The computer-generated vestibular cues, conducting through the headset, provide a user the feel of motion from vestibular nerve stimulation, in turn providing inner ear dysequilibrium and movement sensation. The headset reinforces visual movement sensations by including a means for feeling these sensations.

PRIOR ART

U.S. Pat. No. 5,373,857 (Travers et al.), discloses a head tracker for a virtual reality head set for determining the orientation of the head set relative to the earth's magnetic field includes a magnetic sensor responsive to the earth's magnetic field capable of producing a displacement signal relative to the displacement of the head.

U.S. Pat. No. 5,572,749 (Ogden), teaches a helmet mounting device which allows a helmet for virtual reality displays to be situated comfortably on the user's head.

U.S. Pat. No. 5,737,505 (Shaw et al.), demonstrates a method for entering a virtual reality user's position into the virtual reality environment. The tactile interface system can represent limb movement and allow a user to feel the sensation of touch in virtual reality. The system also provides for the recording of tactile information to accompany audio and visual recordings.

U.S. Pat. No. 5,767,820 (Bassett et al.), shows a head-mounted visual display apparatus having a shell that encases a pair of visual displays and is mounted to a headband. The apparatus provides a video image to an individual wearing the apparatus.

U.S. Pat. No. 5,762,612 (Campbell), teaches the process for vestibular stimulation being synchronized to visual displays for enhacing virtual reality.

U.S. Pat. No. 5,593,432 (Crowther et al.), demonstrates a method and apparatus for alleviating pain and the symptoms of withdrawal of a patient during detoxification by stimulating the nervous system.

U.S. Pat. No. 4,558,703 (Mark), shows an apparatus and method for treating a patient suffering from motion sickness such as air sickness and the like. Relief is provided by producing a sense of gravity acting on the limbs to allow for the perception of "heaviness" as a soothing mechanism.

U.S. Pat. No. 5,515,078 (Grescher et al.), teaches a positional input and display for virtual reality where data from a rotating chair and a joystick are sent to a processor to show and physically enable movement in a virtual world.

U.S. Pat. No. 5,323,468 (Bottesch), demonstrates an arrangement for delivering stereophonic soundwaves through the mastoid bone structure of the human skull. The system bypasses the use of an individual's auditory canals for the purposes of listening by an alternative means.

U.S. Pat. No. 4,918,757 (Janssen et al.), shows a hearing aid support in the form of a headband as a means for aiding the fitting and wearing problems of a user of a hearing aid.

U.S. Pat. No. 4,667,676 (Guinta), teaches a method of evaluating the vestibular system. An involuntary, rapid movement of the eyeball as a response is recorded as an indication of the condition of the vestibular system of the patient.

SUMMARY OF THE INVENTION

The objective of the present invention is to provide greater depth of sensation within virtual environments by providing a headset in both fixed and adjustable forms, sized to accompany virtual reality headgear, and capable of stimulating the vestibular sensory system.

The headset galvanically stimulates the vestibular sensory system by use of conductive electrode pairs capable of optimally compressing against and situating a contactor on the mastoid bone behind each ear and the forehead. Computer generated vestibular cues synchronized with a video display provide galvanic stimulation through the conductors at each respective location on the user's head. The resulting inner ear dysequilibrium amplifies the user's sensation of motion in virtual reality environments.

BRIEF DESCRIPTION OF THE DRAWINGS

FIG. 1 is worn by the user.

FIG. 3 is worn by the user.

DETAILED DESCRIPTION OF THE PREFERRED EMBODIMENT

The invention will now be described in detail in relation to a preferred embodiment and implementation thereof which is exemplary in nature and descriptively specific as disclosed. As is customary, it will be understood that no limitation of the scope of the invention is thereby intended and that the invention encompasses such alterations and further modifications in the illustrated device, and such further applications of the principles of the invention illustrated herein, as would normally occur to persons skilled in the art to which the invention relates.

Figure 1:
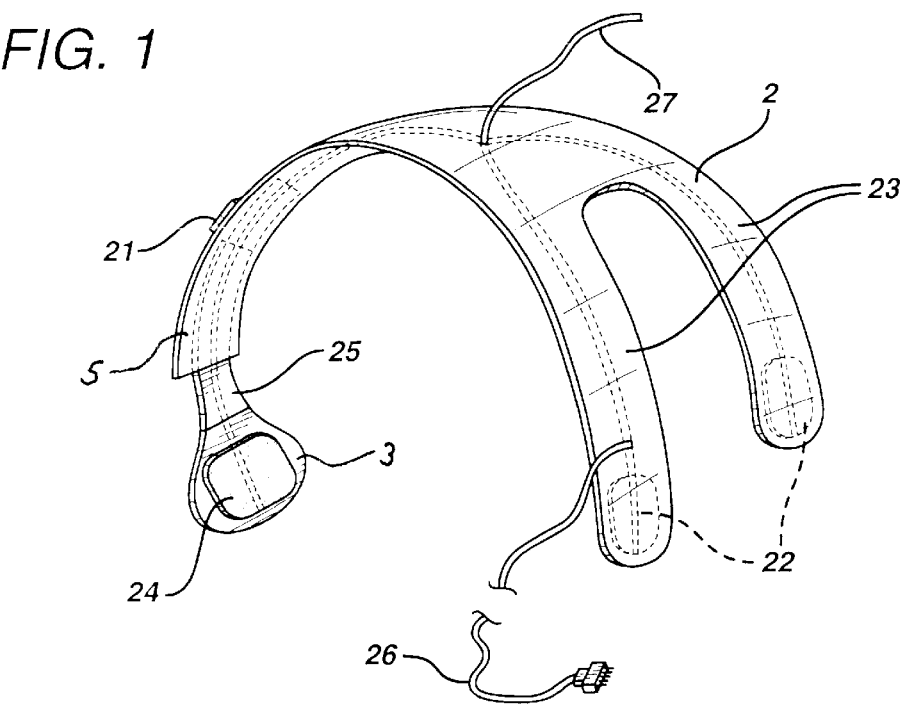
FIG. 1 is a perspective view of an adjustable embodiment of the headset showing the constituent parts.

Thus, with reference now to FIG. 1, there is an embodiment of a type of a three-prong headset 2. The three-prong headset 2 is made of a flexible material and has two side arms 23 and a front arm 5. An adjustable arm 25 can be slid up or down within the front arm 5 and can position a forehead piece 3 securely by friction or by a sliding lock 21. Alternatively, any of a variety of adjustment mechanisms can be employed to enable the simultaneous use of virtual reality headgear similar to that in U.S. Pat. No. 5,767,820. The side arms 23 are capable of flexing to accommodate various head shapes and sizes with a comfortable level of compression. Side arm electrodes 22 are incorporated in the side arms 23, and a ground electrode 24 is incorporated into the forehead piece 3. The ground electrode 24 and the side arm electrodes 22 are made of a conductive material. A galvanic stimulus receiving wire 26 transports the computer-generated vestibular cues that are referenced in U.S. Pat. No. 5,762,612 via the side arm electrodes 22 and the ground electrode 24 to the user, and an infrared receiver 27 is also incorporated on the crown of the headset. Additional sensors such as linear or angular position sensors could also be employed as implemented for the synchronization of the visual stimuli as referenced by U.S. Pat. No. 5,762,612.

Figure 2:
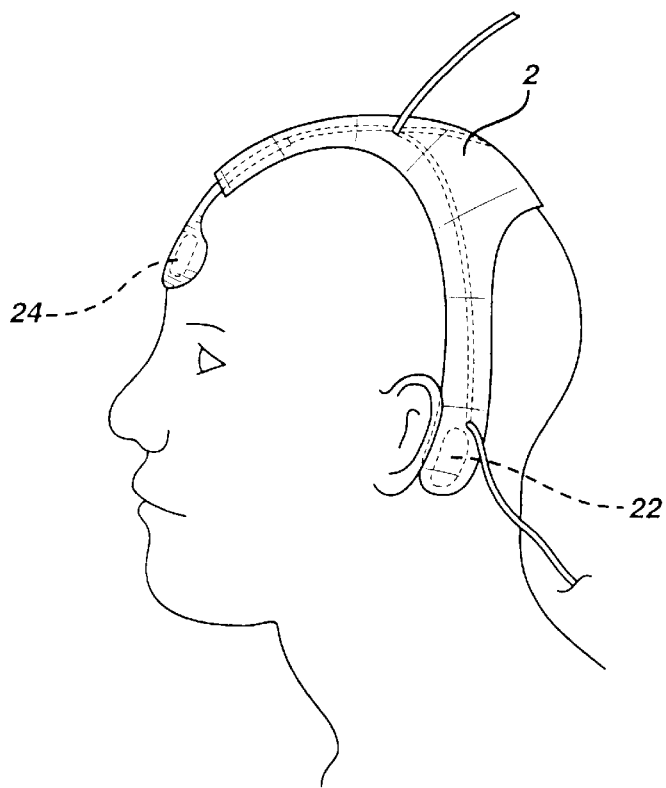
FIG. 2 is a side view demonstrating how

FIG. 2 demonstrates how the three-prong headset 2 is worn by a user. Upon placement of the three-prong headset 2, each side arm electrode 22 is situated on the mastoid bone behind each ear. The ground electrode 24 positions itself against the forehead of the user.

Figure 3:
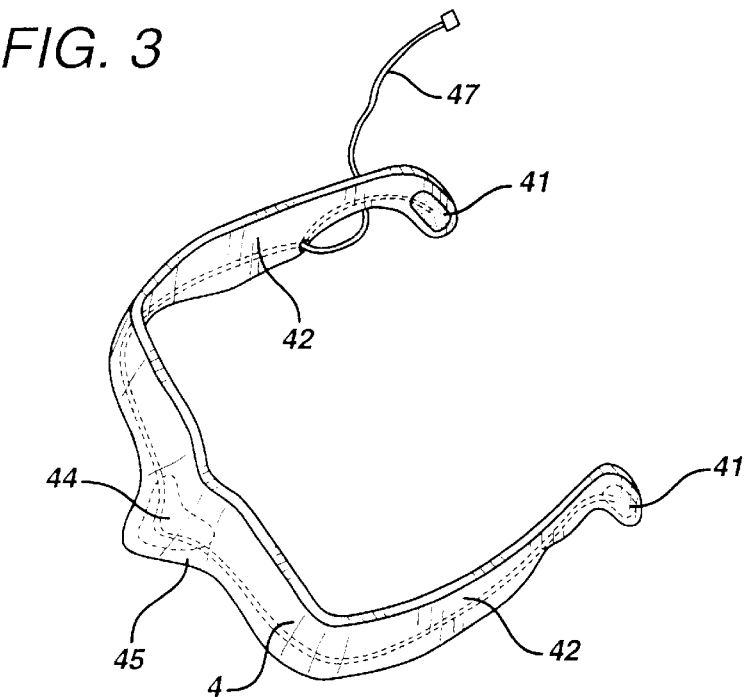
FIG. 3 is a perspective view of a fixed, eyeglasses-type of headset showing the constituent parts.

FIG. 3 shows a simpler embodiment of a two-prong headset 4 which can be made of a flexible, plastic encased foam, or any other flexible material, and can be used simultaneously with virtual reality headgear similar to that in U.S. Pat. No. 5,767,820. The signal electrodes 41 are located at the ends of the two prongs 42. The neutral electrode 44 is incorporated in the front mount piece 45. The signal electrodes 41 and the neutral electrode 44 are made of a conductive material. The signal receiving wire 47 receives the computer generated vestibular cues referenced in U.S. Pat. No. 5,762,612 and transmits the current to the user via the signal electrodes 41 and the neutral electrode 45.

Figure 4:
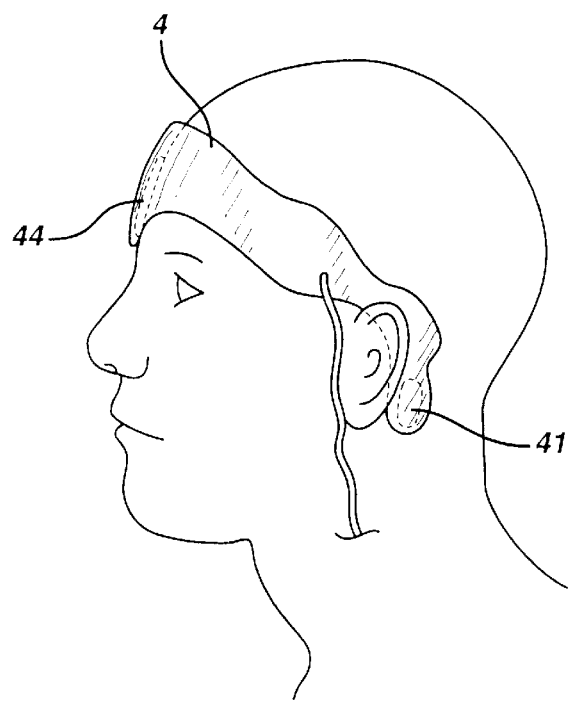
FIG. 4 is a side view demonstrating how

FIG. 4 demonstrates how the two-prong headset 4 is worn by the user. Situated much like the ends of eyeglasses, each of the signal receivers 41 are situated on the mastoid bones of the user. The neutral electrode 44 is positioned on the forehead of the user.

Figure 5:
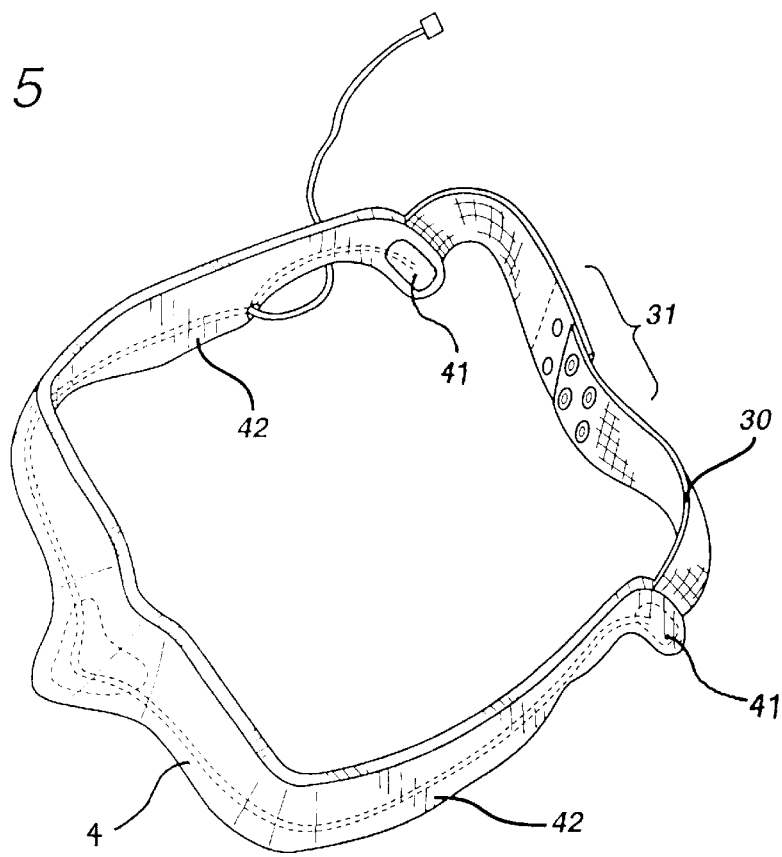
FIG. 5 is a perspective view of an alternative embodiment of FIG. 3 showing the implementation of a securing strap.

FIG. 5 shows an alternative embodiment of the two-prong headset 4 having a connecting strap 30 that connects the ends of the two prongs 42. The strap 30 is fixedly attached to the ends of the two prongs 42 and has a fastening means 31 to allow for various fits by the user and optimal compression of each signal electrode 41.

Figure 6:
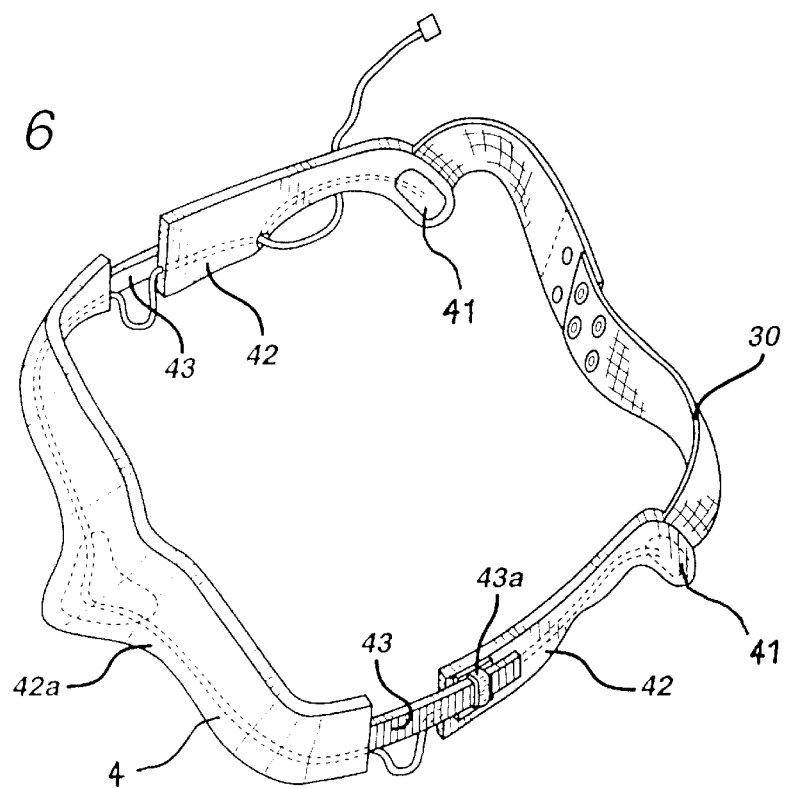
FIG. 6 is a perspective view of the embodiment of FIG. 5 demonstrating the implementation of adjustable ratchet mechanisms for variable adjustment of the headgear.

FIG. 6 shows an embodiment of the two-prong headset 4 employing two ratchet mechanisms 43 that connect a detachable front mount 42a to the side arms 42. The ratchet mechanism 43 allows the two-prong headset 4 to be expandable longitudinally under the ratchet spine 43a to properly situate the signal electrodes 41 around the ear of the user.

I claim:

1. A headgear device for electrical current stimulation of the inner ear of a user by vestibular influence of the mastoid bone associated with a the user,s ears and forehead and capable of being coupled to visual and audio stimuli of virtual reality, comprising:

(a) a three-prong headset adapted to conform to a head of said user concurrent with experiencing said virtual reality, comprising:

(i) a flexible frame having a top adapted to rest on said head of said user;

(ii) two flexible, opposing side arms downwardly curved and disposed from said top adapted to lightly press and encompass said head, each of said side arms having a lower tip, each of said lower tips having a side inner surface;

(iii) an electrode conductor disposed at each of said side inner surfaces adapted to press against said mastoid bone behind each of said ears;

(iv) a front arm downwardly curved and disposed from said top towards said forehead having a cavity and a locking mechanism;

(v) a forehead arm downwardly curved and disposed from inside said cavity having an oval shaped forehead piece, said forehead piece having a front inner surface and a ground electrode disposed at said inner surface adapted to press against said forehead, said forehead arm adapted to moveably fit into said cavity whereby said forehead ann can move vertically and be locked by said locking mechanism, thereby said ground electrode can be positioned to allow for contact to said forehead;

(vi) a galvanic stimulus receiving wire running throughout said frame linking said ground electrode and each of said electrode conductors, and adapted to receive said electrical current, whereby said electrical current is transmitted to and stimulates said inner ear by way of each of said electrode conductors at each of said mastoid bones and is grounded at said ground electrode, thereby causing dysequilibrium to be felt by said user; and, (vii) an infrared detector disposed at said top adapted to detect movement of said head to accompany said virtual reality.

2. A headgear device for electrical current stimulation of the inner ear of a user by vestibular influence of the mastoid bone associated with the user's ears and forehead, and capable of being coupled to visual and audio stimuli of virtual reality, comprising:

(a) a two-prong headset adapted to wrap around a head of said user and accompany said virtual reality, comprising:

(i) a flexible head band having a center and a forehead-facing surface, said center having a lower end triangularly curving downward adapted to centrally situate at said forehead, and having two flexibly protruding arms, each of said protruding arms having ends, each of said ends having a mastoid-facing surface, and each of said ends curved down and adapted to rest behind said ear of said user, thereby said head band is circuxnferentially positioned across said head;

(ii) two signal electrodes disposed at each of said mastoid-facing surfaces adapted to rest against said mastoid bone;

(iii) a neutral electrode disposed at said forehead-facing surface adapted to press against said forehead; and, (iv) a current receiving wire running throughout said headband linking said neutral electrode and each of said signal electrodes, and adapted to receive said electrical current, whereby said electrical cearent is transmitted to and stimulates said inner ear by way of each of said signal electrodes at each of said mastoid bones and is grounded at said neutral electrode, thereby causing dysequilibrium to be felt by said user, (v) a strap fixedly connected to each of said ends and having a fastening means, whereby the compression of said signal electrodes against said mastoid bones can be adjusted; and, (vi) an adjustable ratchet mechanism on each of said prowling arms, whereby said headband can be expanded and retracted to situate on said head, thereby said signal electrodes can be adjusted longitudinally to contact said mastoid bones.

* * * * *

UNITED STATES PATENT AND TRADEMARK OFFICE
CERTIFICATE OF CORRECTION

PATENT NO : 6,077,237
DATED : Jun. 20, 2000
INVENTOR(S): Campbell et al.

It is certified that error appears in the above-identified patent and that said Letters Patent are hereby corrected as shown below:

Column 4, line 60, "user,s" should read --user's--.

Column 5, line 18, "ann" should read --arm--.

Column 6, line 12, "circuxnferentially" should read --circumferentially--.

Column 6, line 22, "cearent" (2nd) should read --current--.

Signed and Sealed this

Twenty-seventh Day of March, 2001

Attest:

NICHOLAS P. GODICI

Attesting Officer

Acting Director of the United States Patent and Trademark Office